United States Patent [19]

Watanabe et al.

[11] 4,447,362

[45] May 8, 1984

[54] PROCESS FOR THE PRODUCTION OF COENZYME Q

[75] Inventors: Kiyoshi Watanabe; Satoshi Ideguchi; Masahiro Ogura; Masahiko Shimada; Hajime Kawaharada, all of Hyogo, Japan

[73] Assignee: Kanegafuchi Kagaku Kogyo Kabushiki Kaisha, Osaka, Japan

[21] Appl. No.: 831,426

[22] Filed: Sep. 8, 1977

[30] Foreign Application Priority Data

Sep. 14, 1976 [JP] Japan .................................. 51-110435

[51] Int. Cl.$^3$ ....................... C07C 46/10; C07C 50/06
[52] U.S. Cl. ............................ 260/396 R; 260/397.25; 435/52; 435/133
[58] Field of Search .................................... 260/396 R

[56] References Cited

U.S. PATENT DOCUMENTS 3,313,831  4/1967  Gale ................................ 260/396 R

FOREIGN PATENT DOCUMENTS 37-9290   2/1962  Japan .
39-26048  11/1964 Japan .

OTHER PUBLICATIONS

A. C. Page, Jr. et al., Archives of Biochemistry & Biophysics, 89, 318-321 (1960).

Primary Examiner—Vivian Garner
Attorney, Agent, or Firm—Armstrong, Nikaido, Marmelstein & Kubovcik

[57] ABSTRACT

A process is disclosed wherein coenzyme Q is prepared from tissues of animals and plants or microbial cells by treating a water suspension of said materials with an alkali, or with an acid and then an alkali, and by extracting the treated suspension with at least one water-immiscible organic solvent followed by recovery of coenzyme Q from the extract.

4 Claims, No Drawings

PROCESS FOR THE PRODUCTION OF COENZYME Q

BACKGROUND OF THE INVENTION

1. Field of the Invention

The present invention relates to a process for the production of coenzyme Q (hereinafter referred to as Co-Q) in high yields from tissues of animals and plants, or microbial cells, which contain Co-Q.

2. Description of the Prior Art

Co-Q occurs in mitochondria of animals and plant tissues, and microbial cells, and is known to play an important role in organisms as an essential factor in the terminal electron transport system. Many reports on the pharmacological and clinical effects of Co-Q have been presented, and remarkable effects on congestive heart failure, coronary insufficiency, muscular dystrophy caused by malnutrition, and anemia have been elucidated. Thus, its value as a medicine has recently increased.

The methods known for the extraction of Co-Q from natural sources include a direct saponification method in which materials containing Co-Q are directly saponified with an alcoholic alkali hydroxide in the presence of an antioxidant such as pyrogallol and thereafter Co-Q is extracted with a hydrophobic solvent such as n-hexane and purified by column chromatography.

In another method, the materials are first extracted, for example, with an organic solvent such as n-hexane, isooctane, acetone, and ethanol, then the extract or the concentrate is purified by column chromatography or saponified with an alcoholic alkali hydroxide in the presence of an antioxidant such as pyrogallol and then Co-Q is extracted with a hydrophobic solvent and purified (Japanese Pat. No. 404804). The direct saponification method, however, has disadvantages such as the necessity of expensive chemicals and the use of large amounts of solvents. On the other hand, in the latter method saponifiable substances such as neutral fats and phospholipids are extracted together with Co-Q. These impurities must be removed by saponifying the extract in the presence of an antioxidant or by complicated purification processes. This method, therefore, also has disadvantages such as high purification costs and low yields because of the use of an antioxidant and the employment of complicated processes.

The present inventors carried out investigations to improve the known methods and to establish a method for obtaining Co-Q in high yield and at a relatively low cost. The present inventors have found that Co-Q is stable to an alkali in water as will be described later. The present inventors further have found that after tissues of animals and plants or microbial cells which contain Co-Q are treated with an alkali, or with an acid and then an alkali, the treatment resulting in the hydrolysis of saponifiable substances such as neutral fats and phospholipids and the disruption of the tissues or cells so that Co-Q becomes readily extractable, non-saponifiable lipids containing Co-Q are obtained in high yields by liquid-liquid extraction with solvents which are separable from water.

SUMMARY OF THE INVENTION

According to the process of the present invention, tissues of animals and plants or microbial cells which contain Co-Q are treated with an alkali, the treated suspension is extracted with at least one water-immiscible organic solvent, and thereafter Co-Q is recovered from the extract. The water suspension can be treated with an acid before the alkali-treatment.

In the known methods for extraction of Co-Q, saponifiable lipids are hydrolyzed in an alcoholic alkali hydroxide, and the presence of an antioxidant such as pyrogallol is essential.

In the method of the present invention, on the other hand, no destruction of Co-Q is observed in spite of the absence of an antioxidant. The reason for the stability of Co-Q in the process of the present invention is considered that the contact of Co-Q with an alkali is prevented because saponification is carried out in a water suspension in the absence of solvents which will dissolve Co-Q and, therefore, the destruction of Co-Q does not proceed.

DESCRIPTION OF PREFERRED EMBODIMENTS

The process of the present invention is applied to tissues of animals and plants and to microbial cells which contain Co-Q. The invention is applicable irrespective of the kinds of Co-Q homologs ($Co-Q_6$–$Co-Q_{10}$) contained in the sources.

As natural sources containing Co-Q, tissues of animals or plants, or cells of yeasts, molds, or bacteria may be used, and the concentration of them in the water suspension can be 10–250 g (dry weight)/l, although 100–200 g/l is preferable for economic reasons.

An acid treatment before the alkali treatment is not always necessary, but often increases the extraction yields of the Co-Q by disrupting the tissues or cells depending on the kinds of sources. As the acid, a mineral acid such as sulfuric, hydrochloric and nitric acid may be used. The acid treatment is usually carried out at a pH of not more than 2, at 60°–150° C. for 0.5–10 hr, and preferably at a pH of not more than 1, at 80°–120° C. for 2–6 hr. The alkali treatment is performed using an alkali metal or alkaline earth metal hydroxide or carbonate, or an alkali metal bicarbonate. For example, sodium or potassium hydroxide, calcium or magnesium carbonate, and sodium or potassium bicarbonate may be used. The alkali treatment is preferably carried out at a pH of not less than 10, at 60°–150° C., for 10 min to 10 hr, and especially at a pH of not less than 13, at 80°–120° C. for 1–5 hr.

For the extraction of Co-Q after the saponification, at least one water-immiscible organic solvent such as n-hexane, isooctane, petroleum ether, dichloroethane, methyl isobutyl ketone, butanol, and ethyl acetate is employed. On occasion, at least one water-miscible organic solvent such as methanol, ethanol, isopropanol, and acetone may be added to the water-immiscible organic solvent in such an amount that the former does not prevent the separation of the latter from the saponified liquid.

The extract is washed with water, dehydrated, and concentrated under reduced pressure. The concentrate is dissolved in a small amount of a hydrophobic solvent such as n-hexane, petroleum ether, and chloroform, and sterols which precipitate on cooling are removed. Co-Q is isolated from the supernatant, for example, by applying it on a column packed with silicagel, alumina, fluorosil, etc. In this process sterols such as ergosterol are readily obtained as by-products.

As mentioned above, the process for extraction and purification of Co-Q of the present invention is simple and obviates the necessity of using expensive antioxidants such as pyrogallol, offering an advantageous method for preparing Co-Q in high yield.

The following examples will illustrate the present invention in detail.

EXAMPLE 1

*Rhodotorula mucilaginosa* AHU 3946 was aerobically cultivated in a medium comprising 30 g glucose, 4 g $KH_2PO_4$, 5 g $(NH_4)_2SO_4$, 0.6 g $MgSO_4.7H_2O$, 10 mg $ZnSO_4.7H_2O$, 100 mg $FeSO_4.7H_2O$, 1 g yeast extract, and 1 l tap water (pH adjusted to 5.0) in a jar fermentor for 62 hr and cells were harvested by centrifugation and washed with water. To 4 l of the cell suspension (dry cell weight; 480 g, Co-Q content: 137 mg) 40 ml conc. $H_2SO_4$ was added. The mixture was heated at 100° C. for 3 hr, allowed to cool, and again heated at 100° C. for 1 hr after adding 220 g NaOH.

After cooling, the reaction mixture was extracted with a mixed solvent comprising 4 l n-hexane and 400 ml isopropanol, and n-hexane layer was separated. This procedure was repeated once. n-Hexane layers were combined and washed with 10 l water 3 times, dried overanhydrous $Na_2SO_4$, and concentrated under reduced pressure. The yield of Co-Q in this step was 0.992. The concentrate was dissolved in a small amount of n-hexane, the solution cooled to 40° C., and precipitated sterols were removed. The supernatant was applied on a column packed with 5 g silica gel, and the elution was carried out with n-hexane-isopropanol (1000:1). Fractions containing Co-Q were combined and concentrated under reduced pressure. The concentrate was dissolved in a small amount of ethanol, and the solution was allowed to cool to give 128 mg of orange-yellow crystals (Yield: 0.934). The product was identified as Co-$Q_{10}$ from mp, paper chromatography, and elementary analysis.

EXAMPLE 2

*Candida novellus* ATCC 20275 was cultivated in the same manner as in Example 1, cells were separated and washed with water. To 4 l of the cell suspension (dry cell weight: 550 g, Co-Q content: 140 mg), 400 ml of 48% (wt./vol.) NaOH solution was added, the mixture was heated at 100° C. for 3 hr and then treated in the same manner as in Example 1 to give 108 mg of crystals (Yield: 0.77).

The product was identified as Co-$Q_9$ from paper chromatography and elementary analysis.

EXAMPLE 3

*Candida utilis* IAM 4200 was cultivated in the same manner as in Example 1. From 4 l of the cell suspension (dry cell weight: 90 g, Co-Q content: 23 mg) Co-Q was extracted and purified in the same manner as in Example 1 to give 19 mg of crystals. The product was identified as Co-$Q_7$ from paper chromatography.

EXAMPLE 4

From 4 l of the cell suspension of 600 g of pressed baker's yeasts (Co-Q content 90 mg), 82 mg of Co-Q crystals were obtained by the same extraction and purification procedure as in Example 1. The product was identified as Co-$Q_6$ from paper chromatography.

EXAMPLE 5

Two kilograms of muscles of fresh beef heart containing 140 mg Co-Q were minced after removal of fats and blood vessels, and homogenized with a Waring blender. The homogenate was made up to a total volume of 4 l with water. From the homogenate 93 mg of Co-Q crystals were obtained in the same manner as in Example 1. The product was identified as Co-$Q_{10}$ from mp and paper chromatography.

EXAMPLE 6

*Agrobacterium tumefaciens* IAM 1037 was cultivated in a medium comprising 30 g glucose, 4 g $KH_2PO_4$, 5 g $(NH_4)_2SO_4$, 0.6 g $MgSO_4.7H_2O$, 10 mg $ZnSO_4.7H_2O$, 100 mg $FeSO_4.7H_2O$, 10 g yeast extract, and 1 l tap water (pH adjusted to 6.0) under the same cultural conditions as in Example 1. From 4 l of the cell suspension (dry cell weight: 120 g, Co-Q content: 31 mg), Co-Q was extracted and purified in the same manner as in Example 1 except that the acid treatment was omitted, and 26 mg of Co-Q crystals were obtained (Yield: 0.84). The product was identified as Co-$Q_{10}$ from paper chromatography.

Although the invention has been described in conjunction with certain preferred embodiments thereof, it is to be understood that it is not intended to be limited thereto, but, instead, includes all those embodiments within the scope and spirit of the appended claims.

We claim:

1. A process for producing coenzyme Q from tissues of animals and plants or microbial cells which contain coenzyme Q and which comprises treating a water suspension of said materials with a mineral acid and then with an alkali in the absence of an alcohol and an antioxidant, extracting the alkali-treated suspension with at least one water-immiscible organic solvent, and isolating coenzyme Q from the extract.

2. The process according to claim 1, wherein the acid is a member selected from the group consisting of sulfuric, hydrochloric and nitric acids.

3. The process according to claim 1, wherein the acid-treatment is carried out at a pH of not more than 2, a temperature of 60°–150° C., and for 0.5–10 hr.

4. The process according to claim 3, wherein the acid-treatment is carried out at a pH of not more than 1, a temperature of 80°–120° C., and for 2–6 hr.

* * * * *